United States Patent [19]
Bader et al.

[11] 4,153,631
[45] May 8, 1979

[54] PROCESS FOR PROCESSING SILVER HALIDE DEVELOPING AGENTS

[75] Inventors: Henry Bader, Newton Center; Charles E. Whitten, Winchester, both of Mass.

[73] Assignee: Polaroid Corporation, Cambridge, Mass.

[21] Appl. No.: 784,933

[22] Filed: Apr. 5, 1977

[51] Int. Cl.$^2$ .............................. C07C 49/44
[52] U.S. Cl. ................................ 260/590 C
[58] Field of Search ............ 260/590 C, 590 D, 590 R

[56] References Cited

U.S. PATENT DOCUMENTS

| | | | |
|---|---|---|---|
| 3,629,336 | 12/1971 | Idelson | 260/590 C |
| 3,772,368 | 11/1973 | Bader et al. | 260/590 C |
| 3,812,191 | 5/1974 | Bader et al. | 260/590 C |
| 3,903,169 | 9/1975 | Bader et al. | 260/590 C |

OTHER PUBLICATIONS

Chatterjea et al., Indian J. Chem., vol. 11, pp. 214–218 (1973).

*Primary Examiner*—James O. Thomas, Jr.
*Assistant Examiner*—James H. Reamer
*Attorney, Agent, or Firm*—Gaetano D. Maccarone; John P. Morley

[57] ABSTRACT

A process for preparing a silver halide developing agent of the formula:

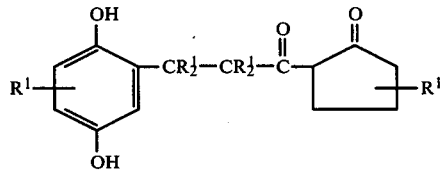

where $R^1$ can be the same or different substituent which will not impair the functionality of the compound as a silver halide developing agent. Specific substituents include hydrogen, alkyl radicals and alkoxy radicals among others. The silver halide developing agents are known as "ligand developers" and are particularly useful in diffusion transfer photographic products and processes.

12 Claims, No Drawings

PROCESS FOR PROCESSING SILVER HALIDE DEVELOPING AGENTS

BACKGROUND OF THE INVENTION

1. Field of the Invention

This invention relates to a process for producing ligand developers of the following formula:

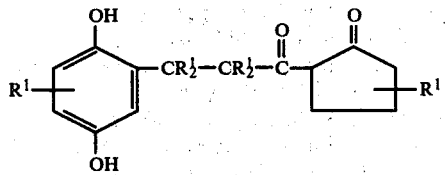

FORMULA 1 where, each $R^1$ can be the same or different substituent chosen from those that will not impair the functionality of the compound as a silver halide developing agent but preferably, each $R^1$ is hydrogen.

2. Description of the Prior Art

Compounds of Formula 1 are known and have been described in at least the following U.S. Patents: U.S. Pat. Nos. 3,629,336; 3,772,368, 3,789,062; 3,812,191 and 3,903,169.

U.S. Pat. Nos. 3,772,368; 3,813,192 and 3,903,169 are particularly directed to methods for producing compounds of Formula 1. For example, U.S. Pat. No. 3,772,368 relates to a method involving reacting a Schiff base anion with a lactone to provide compounds of Formula 1 while U.S. Pat. No. 3,903,169 discloses a method for producing compounds of Formula 1 by way of a condensation reaction between a cyclopentanone anion and a lactone.

The method disclosed in U.S. Pat. No. 3,812,191 is somewhat different from the methods of the patents discussed above involving as it does, the preparation of a compound of the following formula:

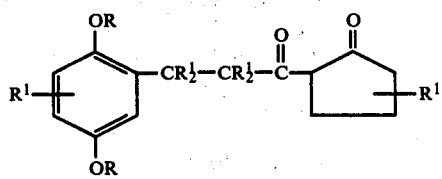

FORMULA 2 where, $R^1$ is as defined before and each R provides a protecting function and is a substituent which can be removed by hydrolysis to provide the compound of Formula 1. Specifically, the method of U.S. Pat. No. 3,812,191 involves the preparation of a "protected" compound of Formula 2 e.g., the compound [3-(2,5-decathyloxyphenyl) propionyl] -2-cyclopentanone and the removal of the protecting groups — the cathyloxy groups—to provide a compound of Formula 1.

According to the method disclosed in referenced U.S. Pat. No. 3,812,191, the cathyloxy groups of the [3-(2,5-dicathyloxyphenyl) propionyl] -2-cyclopentanone are removed by saponifying the protected compound in a substantially non-aqueous, solubilizing medium comprising a solution of an alkali metal hydroxide in an alcohol and acidifying the saponified product to a pH of between about 6.0 to about 7.0 and preferably between about 6.5 to about 7.0. The controlled acidification of the saponified product is an important factor in the method of U.S. Pat. No. 3,812,191 leading to commercially acceptable yields of compounds of Formula 1. For example, if the saponified product is acidified to a pH below 6.0 and particularly to a pH below 3.0, the predominant product is not the compound of Formula 1 but rather a cyclized compound of the following formula:

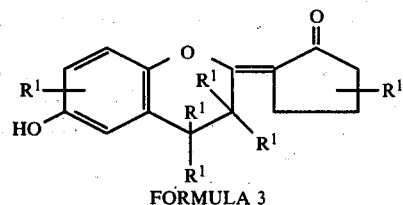

FORMULA 3

In accordance with the practice of the present invention it has been found that the cyclized compounds of Formula 3 are valuable intermediates in the production of developer ligands of Formula 1 since the cyclized compounds can be easily opened up by hydration to provide the compound of Formula 1.

BRIEF SUMMARY OF THE INVENTION

Essentially the process of the present invention involves the following general hydration reaction:

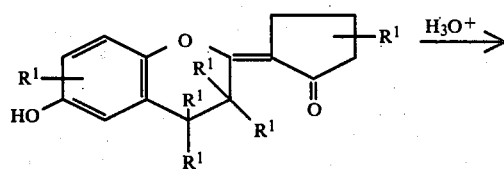

FORMULA 3

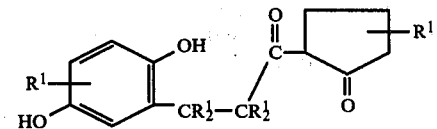

FORMULA 1

According to this invention, cyclized compounds of Formula 3 are hydrated or "opened up" by reacting the cyclized compound with acids in aqueous or partially aqueous media. However, in the particularly preferred embodiment of this invention, the cyclized compounds are hydrated using specific acids in combination with specific reaction solvents or media.

The particularly preferred acids used in the process of this invention are acids of moderate strength having pKa values between about 1.0 and 3.0. Weaker acids such as acetic acid (pKa 4.75) have been found to be extremely slow in "opening up" compounds of Formula 3. Also, the stronger acids such as hydrochloric, sulfuric or trifluoroacetic acid appear to cause degradation of compounds of Formula 3 and provide poor yields of compounds of Formula 1. In accordance with this invention, the particularly preferred acids are organic acids such as chloroacetic acid (pKa 2.85) or dichloroacetic acid (pKa 1.48) but inorganic acids having pKa values between about 1.0 to about 3.0 can also be suitably employed. The amount of acid(s) used is not especially critical but amounts providing at least about 1 mole equivalent of acid per mole of cyclized compound are suitable.

Reaction solvents or media used in the preferred embodiments of this invention are mixtures of water and organic solvents miscible with water. Particularly preferred are mixtures of water with methanol, ethanol, isopropanol, acetone and the like. The ratio of water to organic solvent has been found to be a factor affecting yield and mixtures wherein the water represents from about 30 to about 60% by volume of the total volume of water and organic solvent(s) are particularly suitable. Especially preferred are those mixtures wherein the water represents approximately 50% by volume of the total volume of water and organic solvent(s).

The reaction temperature is not a particularly critical factor and suitable results are obtained by carrying the reaction out at room temperature but higher temperatures can be used if desired.

DESCRIPTION OF PREFERRED EMBODIMENTS

As mentioned, methods for preparing the cyclized compounds of Formula 3 have been disclosed in the art. For example, U.S. Pat. No. 3,812,191 discloses a method in which a compound of Formula 2 was prepared as an intermediate for conversion to the ligand developer of Formula 1. The intermediate is the blocked ligand developer and removal of the "blocking" groups in the defined manner provides the ligand developer of Formula 1. As also disclosed in that patent, cyclized compounds of Formula 3 can be produced by first saponifying the intermediate to remove the "blocking" groups and reacting the saponified product with strong acids. Accordingly, blocked ligand developers of the type described in U.S. Pat. No. 3,812,191 are particularly suitable "precursors" for forming cyclized compounds of Formula 3 which can be easily "opened up" in accordance with the practice of this invention.

Compounds of Formula 2 having protecting groups other than acetoxy or cathyloxy are known and such compounds are suitable "precursors" in the practice of the present invention. For example, U.S. Pat. No. 3,789,062 discloses compounds of Formula 2 where the R group can be alkyl such as methyl or R can be aralkyl such as benzyl. Also, U.S. Pat. No. 3,903,169 discloses compounds of Formula 2 where R can be tetrahydropyranyl. Such compounds of Formula 2 where R is alkyl, aralkyl or tetrahydropyranyl can also be converted to cyclized compounds of Formula 3 by reaction with strong acids or Lewis acids such as hydrochloric or hydrobromic acid, or boron trichloride, boron tribromide, aluminum chloride or aluminum bromide.

U.S. Pat. No. 3,772,368 describes another synthesis for preparing compounds of Formula 1 which involves the preparation of another "precursor" of the following formula:

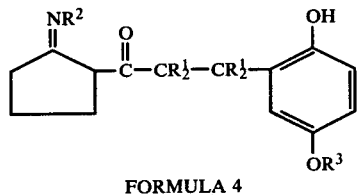

FORMULA 4 where $R^1$ is as defined before, $NR^2$ represents an amino group easily removed under mild conditions to provide a ketone function and $R^3$ is H or an easily removable solublizing protective group such as a 2-tetrahydropyranyl ether. As disclosed in U.S. Pat. No. 3,772,368 the $NR^2$ and $R^3$ groups are removed by hydrolysis to provide compounds of Formula 1 and this hydrolysis can be performed with various organic and inorganic acids. The preferred hydrolysis medium is a mixture of water, tetrahydrofuran and formic acid with the pH of the medium being between about 6 to 7. However, like the compounds of Formula 2 —compounds of Formula 4 can also be converted to cyclized compounds of Formula 3 by reaction with strong acids such as hydrochloric, sulfuric, etc., at pHs below about 3.0. Accordingly, compounds of Formula 4 are also useful "precursors" for providing the cyclized compound of Formula 3 which can be "opened up" according to the process of the present invention to provide ligand developers of Formula 1.

There are special advantages obtained by converting a "precursor" within Formulae 2 and 4 to a cyclized compound and then "opening up" the cyclized compound to provide the ligand developer of Formula 1. The cyclized compounds of Formula 3 are highly crystaline and crystalize well from a wide variety of organic solvents such as ethyl acetate, methanol, ethanol, methyl ethyl ketone, methyl isobutyl ketone and the like. Moreover, the cyclized compounds have a high and relatively well defined melting point. In contrast, the "precursors" have low melting points and solubility characteristics that make purification by crystallization difficult. Accordingly, conversion of the "precursors" to the cyclized compound provides an efficient method for isolating and recovering the "precursors" as cyclized compounds of a high purity which can then be "opened up" by the process of this invention to provide the ligand developers of Formula 1 of a high degree of purity.

Special advantages can also be obtained by using the practice of this invention to purify ligand developers of Formula 1. In accordance with this aspect of the invention, crude or impure ligand developers of Formula 1 are reacted with strong acids to convert the crude — but opened — ligand developer to the cyclized compound of Formula 3. This conversion of the impure ligand developer to the cyclized compound provides an efficient and relatively simple method for isolating the crude or impure ligand developer from the reaction medium as the highly crystalline, high melting cyclized compound. The cyclized compound can then be easily "opened up" according to the practice of this invention to provide compounds of Formula 1 of high purity.

The invention as well as manner of making it and using it will be better appreciated from the following illustrative examples.

EXAMPLE 1

This example illustrates a conversion of a compound of Formula 2 to a cyclized compound of Formula 3.

A solution containing 19.6 g. (0.05 mole) of [3-(2,5-dicathyloxyphenyl)propionyl] -2-cyclopentanone in 100 ml. of n-propanol was deaerated with nitrogen for one hour. A solution of 20.0 g. (0.05 mole) of sodium hydroxide in 500 ml. of n-propanol was similarly deaerated, then added under stirring to the solution of the ligand under nitrogen. The mixture was kept at room temperature for four hours and then cooled to 5° C. Hydrogen chloride gas was passed through the solution until a pH = 1 was obtained on pH indicator paper. Sodium chloride was filtered and propanol was removed under reduced pressure, yielding 12.2 g. (98.2% theory) of the cyclized dehydrated ligand as a yellow solid, 94.0 % pure by VPC. Recystallization from ethyl acetate in 93% yield gave yellow needles, m.p. 203°–206.0° C.; max CH$_3$OH 296 mu, = 18,390; 310 mu, = 17,180; no Ce$^{-4}$ or enol titration; TLC R$_f$ 0.49 ; nmr (in acetone d$_6$) = 8.2 (1H, hydroxyl, non-exchangeable with D$_2$O) = 6.75–7.0 (3H, aromatic), = 1.75–3.40 (9.4H, aliphatic).

EXAMPLE 2

This example illustrates the conversion of a compound of Formula 1 (the ligand developer) to a cyclized compound of Formula 3.

The conversion can be illustrated by the following reaction scheme.

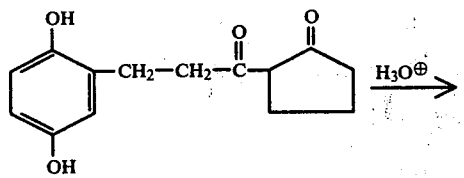

FORMULA 5

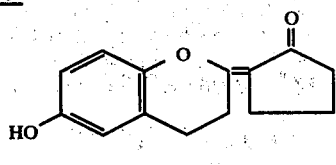

FORMULA 6

A sample of 1 g. of the compound of Formula 5 (90% pure) was dissolved in 15 ml. of methanol and deaerated with nitrogen. To this, 1.5 g. of a 50% solution of sodium hydroxide, previously deaerated, was added and the solution was allowed to return to room temperature (2 hours) after a slight exotherm. The solution was then cooled to 5°–10° C. and 15 ml. of concentrated hydrochloric acid were added. The solution was extracted with ethyl acetate, the organic layer was dried over magnesium sulfate, and solvent removed under vacuum. The solid residue was analyzed by VPC and found to be 93.2% pure cyclic ligand of Formula 6.

EXAMPLE 3

This example illustrates a process of the present invention for "opening up" cyclized compounds of Formula 3.

To a solution of 2.65 g. of chloroacetic acid (28.0 m mol) in 20 ml. of 1:1 ethanol/water was added 1.0 g. (4.35 m mol) of cyclized, dehydrated ligand of Example 1. The mixture was stirred under nitrogen at room temperature for 12 hours by which time a homogeneous solution had been obtained. After an additional 36 hours, the solution was poured into 50 ml. of 1M sodium bicarbonate and extracted with three 50 ml. portions of ethyl acetate. The combined organic phases were dried over sodium sulfate, and the solvent was removed in vacuo to leave 0.980 g. of a yellow solid. Enol titration (0.1 N NaOH, in methanol) indicated that the crude product contained 87.2% by weight of the compound represented by Formula 5 (79% yield). Analysis of the crude product by TLC (10% MeOH in C$_6$H$_6$ Silica Gel 60, F-254, E. Merck, Darmstadt) showed the presence of only a trace impurity other than residual cyclized ligand.

EXAMPLE 4

The example illustrates another process of the present invention for "opening up" a cyclized compound of Formula 3.

To a solution of 3.2 g (25.0 m mol) of dichloroacetic acid in 25 ml. of 1:1 isopropanol/water was added 1.00 g. (4.35 m mol) of cyclized, dehydrated ligand of Example 1. The mixture was stirred under nitrogen for 48 hours, and the product was isolated by a procedure identical to that described in Example 3. Evaporation of the solvent in vacuo left 0.981 g. of a yellow solid. Enol titration (0.1 N NaOH in methanol) indicated that the product contained 78.7% by weight of the compound represented by Formula 5 (71% yield). Analysis of the product by TLC again indicated only trace impurities other than the cyclized ligand.

Since certain changes can be made in the above description of the process without departing from the spirit or scope of the invention defined in the claims, it is intended that all matter contained in the above description shall be interpreted as illustrative and not in a limiting sense.

What is claimed is:

1. A process which comprises the step of hydrating a cyclized compound of the Formula:

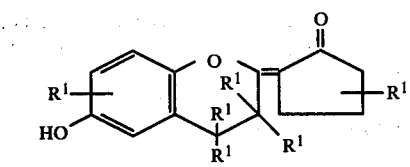

in a medium comprising a mixture of water and a water miscible organic solvent where the water in said medium comprises from about 30% to about 60% by volume of the total volume of water and solvent, and an acid having a pKa between about 1.0 and about 3.0 in an amount sufficient to provide at least about 1 mole equivalent of acid per mole of cyclized compound to provide a compound of the Formula:

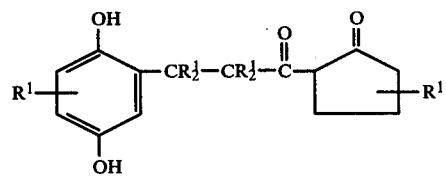

where R$^1$ can be the same or different substituent chosen from those substituents which do not impair the functionality of said compound as a silver halide developer.

2. A process of claim 1 where said acid is chosen from the group consisting of chloroacetic acid, dichloroacetic acid and mixtures thereof.

3. A process of claim 1 where said miscible organic solvent is chosen from the group consisting of methanol, ethanol, isopropanol, acetone and mixtures thereof.

4. A process of claim 1 where the water in said medium comprises about 50% by volume of the total volume of water and solvent.

5. A process which comprises the steps of hydrating a cyclized compound of the Formula:

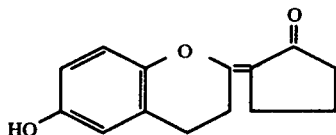

in a medium comprising a mixture of water and an organic miscible solvent where the water in said medium comprises from about 30% to about 60% by volume of the total volume of water and solvent, and an acid having a pKa between about 1.0 and about 3.0 in an amount sufficient to provide at least about 1 mole equivalent of acid per mole of cyclized compound to provide a compound of the Formula:

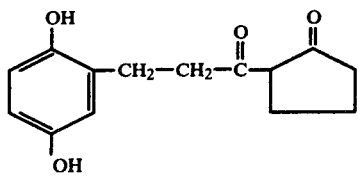

6. A process of claim 5 where said acid is chosen from the group consisting of chloroacetic acid, dichloroacetic acid and mixtures thereof.

7. A process of claim 5 where said miscible organic solvent is chosen from the group consisting of methanol, ethanol, isopropanol, acetone and mixtures of these.

8. A process of claim 5 where the water in said medium comprises about 50% by volume of the total volume of water and solvent.

9. A process which comprises the step of hydrating a cyclized compound of the Formula:

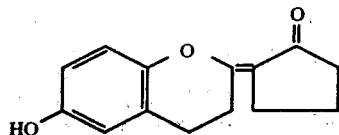

in a medium comprising a mixture of water and a water miscible organic solvent where the amount of water is between about 30% and about 60% by volume of total volume of the water and solvent chosen from the group consisting of methanol, ethanol, isopropanol, acetone and mixtures of these and an acid selected from the group consisting of chloroacetic acid, dichloroacetic acid or mixtures thereof in an amount sufficient to provide at least about 1 mole equivalent of acid per mole of cyclized compound to provide a compound of the Formula:

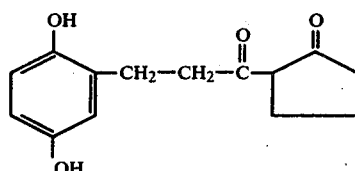

10. A process of claim 9 where the water in said medium comprises about 50% by volume of the total volume of water and solvent.

11. A process of claim 9 where said acid is chloroacetic acid.

12. A process of claim 9 where said acid is dichloroacetic acid.

* * * * *